(12) United States Patent
Anttila

(10) Patent No.: US 8,772,353 B2
(45) Date of Patent: *Jul. 8, 2014

(54) METHOD FOR ENHANCING THE BIOAVALABILITY OF OSPEMIFENE

(71) Applicant: Hormos Medical Ltd., Turku (FI)

(72) Inventor: Markku Anttila, Turku (FI)

(73) Assignee: Hormos Medical Ltd., Turku (FI)

( * ) Notice: Subject to any disclaimer, the term of this patent is extended or adjusted under 35 U.S.C. 154(b) by 0 days.

This patent is subject to a terminal disclaimer.

(21) Appl. No.: 13/904,818

(22) Filed: May 29, 2013

(65) Prior Publication Data

US 2013/0324614 A1    Dec. 5, 2013

Related U.S. Application Data

(63) Continuation of application No. 13/543,166, filed on Jul. 6, 2012, now Pat. No. 8,470,890, which is a continuation of application No. 10/777,211, filed on Feb. 13, 2004, now Pat. No. 8,236,861.

(51) Int. Cl.
*A61K 31/075* (2006.01)

(52) U.S. Cl.
USPC ............................ 514/720; 514/721

(58) Field of Classification Search
CPC ............. A61K 31/075; A61K 31/085
USPC ................................. 514/720, 721
See application file for complete search history.

(56) References Cited

U.S. PATENT DOCUMENTS

| | | | |
|---|---|---|---|
| 5,605,700 | A | 2/1997 | Degregorio et al. |
| 5,750,576 | A | 5/1998 | DeGregorio et al. |
| 5,912,273 | A | 6/1999 | Degregorio et al. |
| 6,219,674 | B1 | 4/2001 | Classen |
| 6,245,819 | B1 | 6/2001 | Halonen et al. |
| 6,387,920 | B2 | 5/2002 | Huebner et al. |
| 6,584,472 | B2 | 6/2003 | Classen |
| 6,984,665 | B2 | 1/2006 | Blom et al. |
| 7,653,639 | B2 | 1/2010 | Classen |
| 8,236,861 | B2 | 8/2012 | Anttila |
| 8,470,890 | B2 | 6/2013 | Markku |
| 2005/0187301 | A1 | 8/2005 | Lehtola et al. |
| 2005/0187302 | A1 | 8/2005 | Blom et al. |
| 2005/0272825 | A1 | 12/2005 | Blom et al. |
| 2006/0293294 | A1 | 12/2006 | Blom et al. |
| 2007/0104742 | A1 | 5/2007 | Lehtola et al. |

FOREIGN PATENT DOCUMENTS

| | | |
|---|---|---|
| EP | 1 713 458 B1 | 10/2006 |
| WO | WO 96/07402 | 3/1996 |
| WO | WO 9607402 A1 | 3/1996 |
| WO | WO 9732574 | 9/1997 |
| WO | WO 02/07718 | 1/2002 |
| WO | WO 03/103649 | 12/2003 |
| WO | WO 03/103649 A1 | 12/2003 |

OTHER PUBLICATIONS

Ohkura (JMAJ 47(4): 183-185 (2004).*
L.E. Holodov, V.P. Yacovelev, "Clinical Pharmacokinetic", M., Medicine, 1985, p. 87. Translated summary included.
D.M. Biskobing, Novel therapies for osteoporosis, Expert Opinion Invest. Drug 2003 12(4): 611-621.
www.endocrineweb.com/osteoporosis/treatment.htmlWeb, (1998).
www.surgeongeneral.gov/library/bonehealth/chapter_9.html, Feb. 24, 2005 (1-43).
Familydoc.org (2000) 1page.
Vasu, Council of Medical Research (2000) p. 1-5.
Melander et al., Eur. J. Clinical Pharmacology 1978, 14, 441-444.
M. Anttila, "Effect of food on the pharmacokinetics of 'Toremifene," Head and Neck Cancer, European Journal of Cancer, 1997, vol. 33, Supp. 8, 1144 p. 8253.
L. Kangas, Biochemical and pharmacological effects of toremifene metabolites, Cancer Chemotherapy and Pharmacology, 1990, vo. 27, pp. 8-12.
V.C. Jordan, "Antiestrogens and Selective Estrogen Receptor Modulators as Multifunctional Medicines, 2. Clinical Considerations and New Agents," Journal of Medicinal Chemistry, Mar. 27, 2003, vol. 46, No. 7, pp. 1081-1111.
Malcolm Rowland, et al., "Clinical Pharmacokinetics, Concepts and Applications", 3rd Edition, Williams & Wilking, 1995, pp. 120-121.
FDA Guidance for Industry Food, Effect Bioavailability and Fed Bioequivalence Studies, 2002, pp. 1-11.

(Continued)

*Primary Examiner* — Shirley V Gembeh
(74) *Attorney, Agent, or Firm* — Brinks Gilson & Lione; William Boudreaux

(57) ABSTRACT

This invention relates to a method for enhancing the bioavailability of a therapeutically active compound of the formula (I)

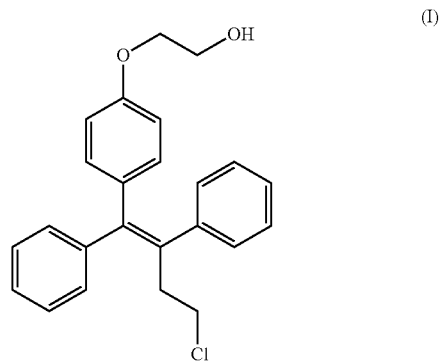

(I)

or a geometric isomer, a stereoisomer, a pharmaceutically acceptable salt, an ester thereof or a metabolite thereof, wherein said compound is administered orally to the individual in connection with the intake of food.

19 Claims, 2 Drawing Sheets

(56) References Cited

OTHER PUBLICATIONS

Christopher J. H. Porter, et al., Lipid Based Formulations for Oral Administration, J. of Receptor & Signal Transduction Research, 21(2&3), 215-257 (2001), pp. 215-257.

Kauffman RF, Bryant HU; "Selective estrogen receptor modulators," *Drug News Perspect.*, 1995, v. 8, pp. 531-539.

H.G. Burger, Selective Oestrogen Receptor Modulators, 53 Hormone Research Suppl. 3:25-29 (2000).

M.A. Seoud et al., Gynecologic tumors in tamoxifen-treated women with breast cancer, 82 Obstetrics & Gynecology 165-69 (1993).

M. Anttila et al., Pharmacokinetics of Toremifene, 36 J. Steroid Biochemistry 249-52 (1990).

T.-L. Yue et al., Selective Estrogen Receptor Modulator Idoxifene Inhibits Smooth Muscle Cell Proliferation, Enhances Reendothelialization, and Inhibits Neointimal Formation In Vivo After Vascular Injury, 102 Circulation III-281-88 (2000).

Ospemifene, 29 Drugs of the Future 38-44 (2004).

K.C. Morello et al., Pharmacokinetics of Selective Estrogen Receptor Modulators, 42 Clinical Pharmacokinetics 361-72 (2003).

M.W. DeGregorio et al., Pharmacokinetics of (deaminohydroxyl)toremifene in humans: a new, selective estrogen-receptor modulator, 56 European J. Clinical Pharmacology 469-75 (2000).

J.E. Axelson et al., "Food increases the bioavailability of propafenone," 23 Br. J. Clin. Pharmacol. 735-741 (1987).

P.A. Winstanley et al., "The effects of food on drug bioavailability," 28 Br. J. Clin. Pharmacol. 621-628 (1989).

\* cited by examiner

METHOD FOR ENHANCING THE BIOAVALABILITY OF OSPEMIFENE

CROSS REFERENCE TO RELATED APPLICATIONS

This application is a continuation application of U.S. patent application Ser. No. 13/543,166, filed Jul. 6, 2012, now allowed, which is a continuation application of U.S. patent application Ser. No. 10/777,211, filed Feb. 13, 2004, now U.S. Pat. No. 8,236,861, which is incorporated by reference herein.

FIELD OF THE INVENTION

This invention relates to a method for enhancing the bioavailability of ospemifene and closely related compounds by oral administering of said compounds in connection with food intake.

BACKGROUND OF THE INVENTION

The publications and other materials used herein to illuminate the background of the invention, and in particular, cases to provide additional details respecting the practice, are incorporated by reference.

"SERM"s (selective estrogen receptor modulators) have both estrogen-like and antiestrogenic properties (Kauffman & Bryant, 1995). The effects may be tissue-specific as in the case of tamoxifen and toremifene which have estrogen-like effects in the bone, partial estrogen-like effect in the uterus and liver, and pure antiestrogenic effect in breast cancer. Raloxifene and droloxifen are similar to tamoxifen and toremifene, except that their antiestrogenic properties dominate. Based on the published information, many SERMs are more likely to cause menopausal symptoms than to prevent them. They have, however, other important benefits in elderly women: they decrease total and LDL cholesterol, thus deminishing the risk of cardiovascular diseases, and they may prevent osteoporosis and inhibit breast cancer growth in postmenopausal women. There are also almost pure antiestrogens under development.

Ospemifene is the Z-isomer of the compound of formula (I)

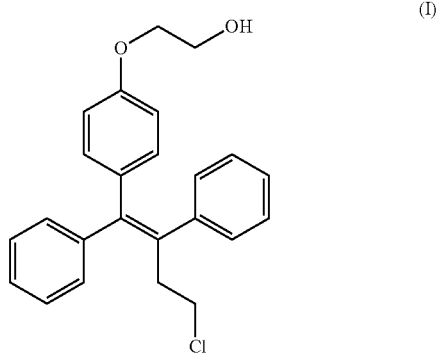 [SMILES: OCCOc1ccc(/C(=C(/CCCl)c2ccccc2)c2ccccc2)cc1]

is one of the main metabolites of toremifene, and is known to be an estrogen agonist and antagonist (Kangas, 1990; International patent publications WO 96/07402 and WO 97/32574). The compound is also called (deaminohydroxy) toremifene and is also known under the code FC-1271a.

Ospemifene has relatively weak estrogenic and antiestrogenic effects in the classical hormonal tests (Kangas, 1990). It has anti-osteoporosis actions and it decreases total and LDL cholesterol levels in both experimental models and in human volunteers (International patent publications WO 96/07402 and WO 97/32574). It also has antitumor activity in an early stage of breast cancer development in an animal breast cancer model. Ospemifene is also the first SERM which has been shown to have beneficial effects in climacteric syndromes in healthy women. The use of ospemifene for the treatment of certain climacteric disorders in postmenopausal women, namely vaginal dryness and sexual dysfunction, is disclosed in WO 02/07718. The published patent application WO 03/103649 describes the use of ospemifene for inhibition of atrophy and for the treatment or prevention of atrophy-related diseases or disorders in women, especially in women during or after the menopause. A particular form of atrophy to be inhibited is urogenital atrophy, which can be divided in two subgroups: urinary symptoms and vaginal symptoms.

Ospemifene is a highly lipophilic compound. Although ospemifene has an excellent tolerability, a problem is the low aqueous solubility and rather low bioavailability. Therefore, when administered orally, the recommended daily dose is about 60 mg or more.

There is a great need for providing administering methods resulting in improved bioavailability of ospemifene, and therefore the effect of food intake on ospemifene was studied.

OBJECT AND SUMMARY OF THE INVENTION

An object of the present invention is to provide an improved oral method of administering ospemifene, where the bioavailability of the drug is essentially increased.

Thus, the invention concerns a method for enhancing the bioavailability of a compound of the (I)

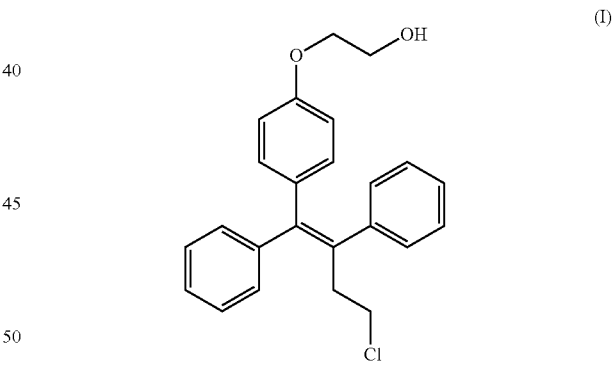

or a geometric isomer, a stereoisomer, a pharmaceutically acceptable salt, an ester thereof or a metabolite thereof, wherein said compound is administered to the individual in connection with the intake of food.

DETAILED DESCRIPTION OF THE INVENTION

Figure 1:
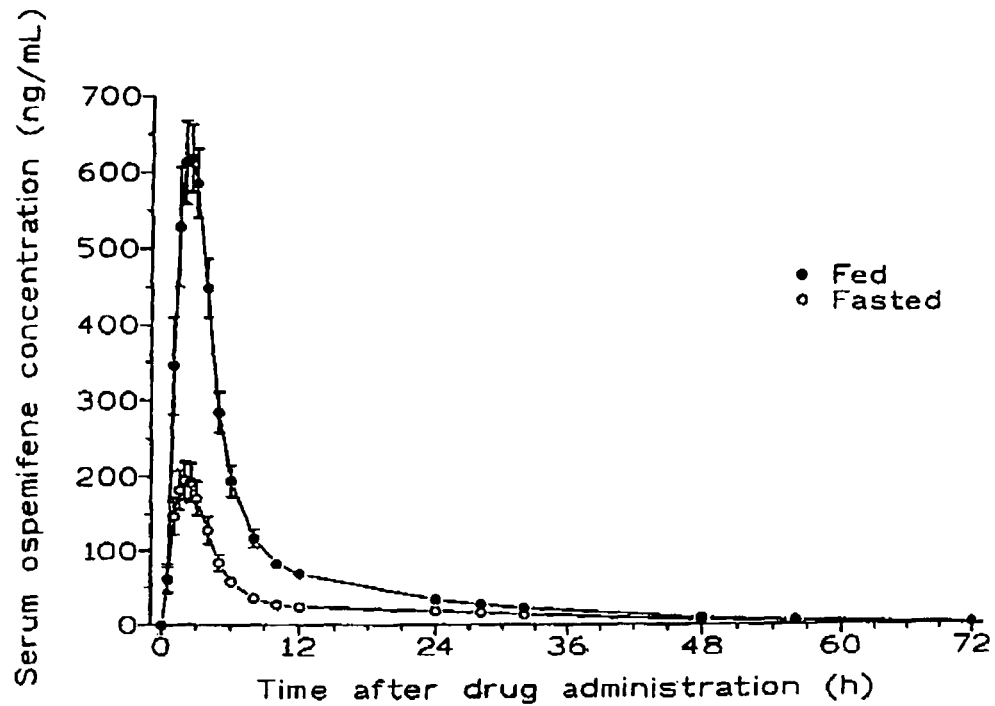
FIG. 1 shows the mean serum concentration in male individuals (n=24) of ospemifene versus time following the administration of 60 mg ospemifene tablet in fasted condition (open circles) and after a high caloric, high-fat meal (filled circles).

Although it is previously known that certain lipophilic drugs may benefit from administering the drug in connection with food intake, the strength of the effect of food intake upon the ospemifene bioavailability obtained in the present investigations was very surprising. Particularly compared to the behaviour of other SERMs, the food effect on ospemifene is remarkable. It was found (Anttila M., 1997) that the intake of food did not have any positive effect on the bioavailability of toremifene, which like ospemifene also has a low aqueous solubility. It was observed that food intake in fact retarded the absorption of toremifene. It has also been reported that the administration of raloxifene, another SERM, together with a standardized high-fat meal increases the absorption of raloxifene slightly, but that it does not lead to clinically meaningful changes in systemic exposure. While food intake causes only a 20% increase of raloxifene absorption, the effect on ospemifene absorption is a 2-3 fold increase.

The term "food" shall be understood to cover any edible foodstuff having a nutritional value as an energy supplier. Thus the food can be solid, semisolid or liquid substance comprising one or more of the basic ingredients carbohydrates, fats and proteins.

Surprisingly, a high percentage of fats or a high energy value in the food intake is not crucial for obtaining a high bioavailability for ospemifene. Neither is the amount of food intake crucial for the beneficial effect.

It is believed that the secretion of bile acids may play an important role in the improved bioavailability, and therefore any foodstuff being capable of causing secretion of bile acids is expected to work.

The drug is considered to be administered in connection with the intake of food if the drug is administered at a time point shortly before the start of the food intake, during the food intake or in a relatively short time after the food intake is completed. A preferable time range is defined to begin 1 hour before starting the food intake and to end 2 hours after starting the food intake. More preferably, the drug is administered at a time point which is in the range defined to begin at a time point during the food intake and to end 1 hour after the food intake was started. Most preferably, the drug is administered during the food intake or at a time point which is no later than 0.5 hour after starting the food intake.

The method of enhancing the bioavailability of ospemifene and related compounds according to this invention is particularly useful when treating women during or after the menopause. However, the method according to this invention is not restricted to women in this age group.

The term "metabolite" shall be understood to cover any ospemifene or (deaminohydroxy)toremifene metabolite already discovered or to be discovered. As examples of such metabolites can be mentioned the oxidation metabolites mentioned in Kangas (1990) on page 9 (TORE VI, TORE VII, TORE XVIII, TORE VIII, TORE XIII), especially TORE VI and TORE XVIII, and other metabolites of the compound.

The most important metabolite of ospemifene 4-hydroxy-ospemifene, which has the formula

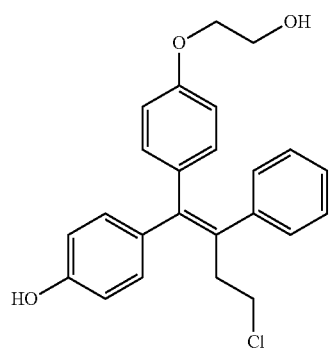 [SMILES: OCCOc1ccc(/C(=C(/CCCl)c2ccccc2)c2ccc(O)cc2)cc1]

The use of mixtures of isomers of compound (I) shall also be included in this invention.

The method of enhancing bioavailability is useful in any application of ospemifene, especially when the compound is used for treatment or prevention of osteoporosis or for treatment or prevention of symptoms related to skin atrophy, or to epithelial or mucosal atrophy.

A particular form of atrophy which can be inhibited by administering of ospemifene is urogenital atrophy. Symptoms related to urogenital atrophy can be divided in two subgroups: urinary symptoms and vaginal symptoms. As examples of urinary symptoms can be mentioned micturation disorders, dysuria, hematuria, urinary frequency, sensation of urgency, urinary tract infections, urinary tract inflammation, nocturia, urinary incontinence, urge incontinence and involuntary urinary leakage.

As examples of vaginal symptoms can be mentioned irritation, itching, burning, maladorous discharge, infection, leukorrhea, vulvar pruritus, feeling of pressure and postcoital bleeding.

According to previous data, the optimal clinical dose of ospemifene is expected to be higher than 25 mg daily and lower than 100 mg daily. A particularly preferable daily dose has been suggested in the range 30 to 90 mg. At the higher doses (100 and 200 mg daily), ospemifene shows properties more similar to those of tamoxifen and toremifene. Due to the enhanced bioavailability according to the method of this invention, it can be predicted that the same therapeutical effect can be achieved with doses lower those recommended earlier.

The invention will be disclosed more in detail in the following non-restrictive Experimental Section.

Experimental Section

Two clinical studies were carried out in order to assess the bioavailability of ospemifene in healthy male subjects after intake of high caloric content (860 kcal) and high-fat breakfast compared to bioavailability of ospemifene administered in fasted condition (study A). In a separate study (study B), the bioavailability of ospemifene after intake of low caloric content (300 kcal), low-fat breakfast was assessed and the results were compared to those obtained in study A (i.e. ospemifene bioavailability after intake of high caloric, high-fat breakfast or after ospemifene administering in fasted condition).

Study A

In study A, 24 healthy male volunteers (mean age 23.8 years, mean BMI 22.8 kg/m$^2$) received single oral doses of 60 mg ospemifene, once under fed condition after consuming a standardised high-fat, high caloric breakfast, and once after an overnight fast. Blood samples for pharmacokinetic assessments were drawn during 72 hours at each study period. A washout period between the two treatments was at least 2 weeks. The breakfast consisted of the following ingredients: two eggs fried in butter (50 g), two strips of bacon (34 g), two slices of toast with butter (50 g), 60 g hash brown potatoes and 240 ml of whole milk (percentage of fat=3.5%). The meal provided approximately 150, 170 and 540 kcal from protein, carbohydrate and fat, respectively.

Ospemifene Administration in Connection with High Caloric, High-Fat Test Meal:

Following an overnight fast of at least 10 hours at the study site, the subjects were given the test meal described above 30 minutes before ospemifene dosing (60 mg tablet). The meal had to be consumed over the 30 minutes, immediately followed by administration of ospemifene.

Ospemifene Administration in Fasted Condition:

Following an overnight fast of at least 10 hours at the study site, the subjects were given one ospemifene tablet (60 mg) with 240 ml of water. No food was allowed for at least 4 hours after the ospemifene dose.

Results from Study A

A substantial effect of food intake was observed on the bioavailability of ospemifene and its main metabolite 4-hydroxy-ospemifene. FIG. 1 shows the mean serum concentration of ospemifene versus time following the administration of 60 mg ospemifene tablet in fasted condition (open circles) and after a high caloric, high-fat meal (filled circles). The results of this study showed clearly that the ospemifene bioavailability was enhanced by concomitant ingestion of ospemifene and a meal.

Due to the surprising and promising results of this study it was decided to carry out a second study (study B below) to find out the effect of a low caloric, low-fat meal on the bioavailability of ospemifene.

Study B

In study B, 12 healthy male volunteers (mean age 23.8 years, mean BMI 22.3 kg/m$^2$) of the 24 subjects in study A were subjected to ospemifene administering in combination with the intake of a low caloric, low-fat meal. The results were compared to those obtained in study A for the same individuals.

Ospemifene Administering in Connection with Low Caloric, Low-Fat Meal:

The composition of the light breakfast (approximately 300 kcal) was as follows: two slices of toast with margarine (5 g, fat content 60%), 6 slices (30 g) of cucumber, 240 ml skimmed (non-fat) milk and 100 ml orange juice. The test meal provided approximately 50, 180 and 70 kcal from protein, carbohydrate and fat, respectively.

Following an overnight fast of at least 10 hours at the study site, the subjects were given the test meal described above 30 minutes before ospemifene dosing (60 mg tablet). The meal had to be consumed over the 30 minutes, immediately followed by administration of ospemifene.

Results from Study B

Figure 2:
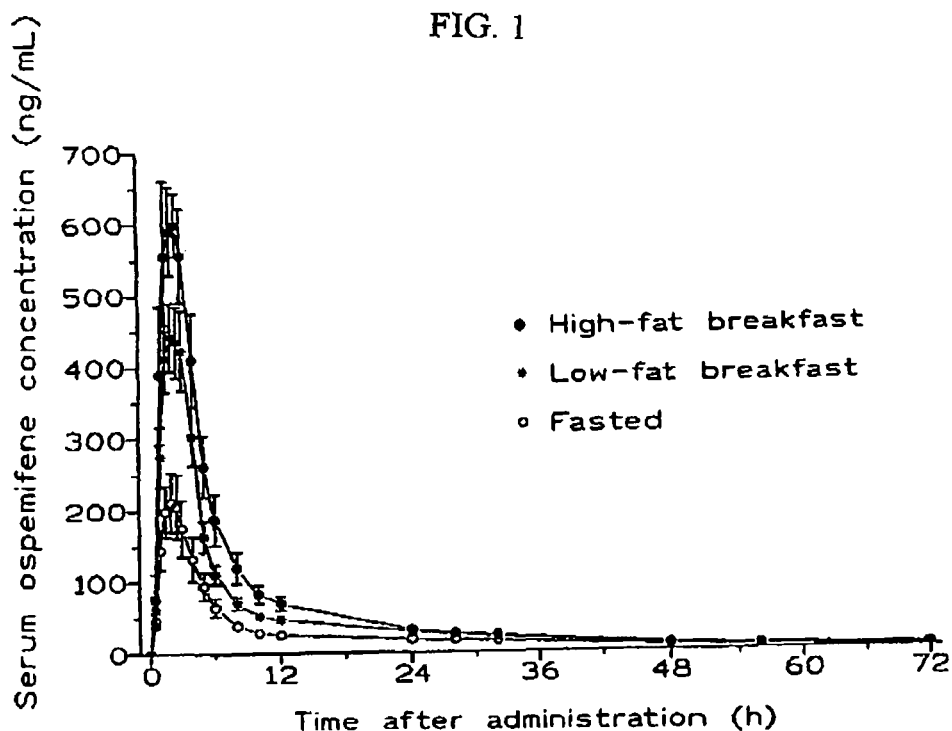
FIG. 2 shows the mean serum concentration in male individuals (n=12) of ospemifene versus time following the administration of 60 mg ospemifene tablet in fasted condition (open circles); after a high caloric, high-fat meal (filled circles) and after a low caloric, low-fat meal (stars).
Figure 3:
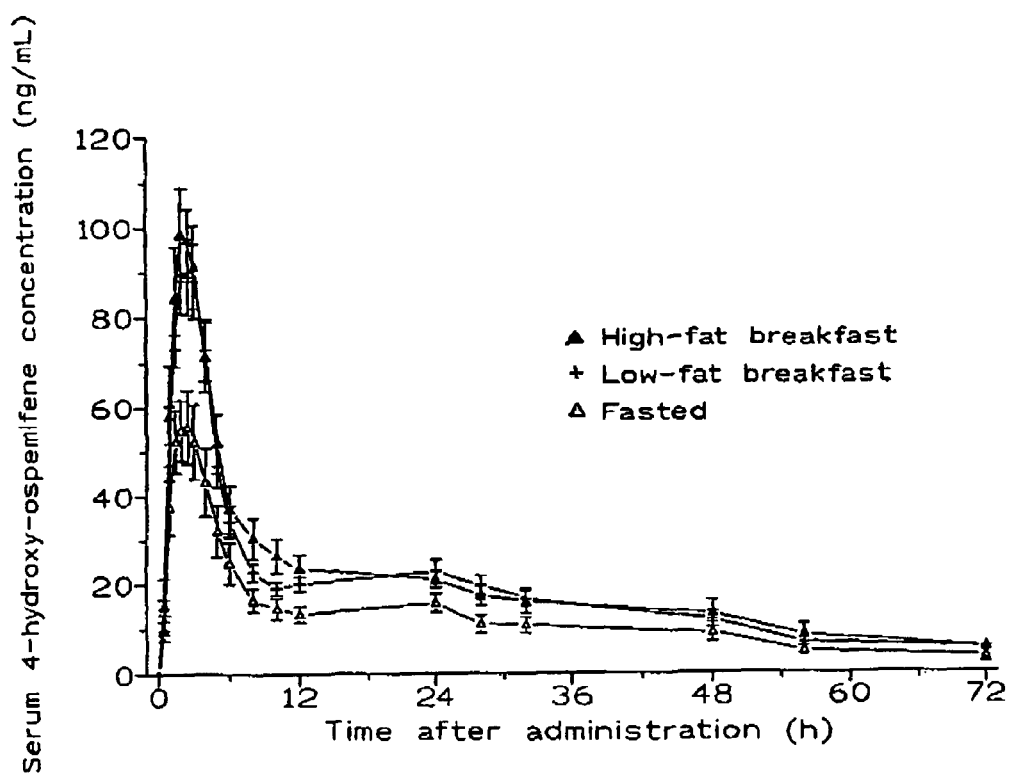
FIG. 3 shows the mean serum concentration in male individuals (n=12) of the ospemifene metabolite 4-hydroxy-ospemifene versus time following the administration of 60 mg ospemifene tablet in fasted condition (open triangles); after a high caloric, high-fat meal (filled triangles) and after a low caloric, low-fat meal (crosses).

FIG. 2 shows the mean serum concentration of ospemifene versus time following the administration of 60 mg ospemifene tablet in fasted condition (open circles; data obtained from study A); after a high caloric, high-fat meal (filled circles; data obtained from study A) and after a low caloric, low-fat meal (stars). FIG. 3 shows the mean serum concentration of the ospemifene metabolite 4-hydroxy-ospemifene versus time following the administration of 60 mg ospemifene tablet in fasted condition (open triangles; data obtained from study A); after a high caloric, high-fat meal (filled triangles; data obtained from study A) and after a low caloric, low-fat meal (crosses).

The results of this study showed clearly that the bioavailability of ospemifene was also enhanced by concomitant ingestion of ospemifene and a low caloric, low-fat meal. Although the fat content of the low-fat meal was much lower than that of the high-fat meal, the bioavailability of ospemifene was only slightly lower for the low-fat meal. Therefore it can be concluded that the effect of food on the ospemifene bioavailability is not dependent on the fat content of the meal ingested. Instead, stimulation of bile flow due to meal ingestion may enhance the solubilisation of ospemifene.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

BIBLIOGRAPHY

Anttila M. Effect of food on the pharmacokinetics of toremifene. Eur J Cancer, 1997; 33, suppl 8: 1144, 1997.

Kangas L. Biochemical and pharmacological effects of toremifene metabolites. Cancer Chemother Pharmacol 27:8-12, 1990.

Kauffman R F, Bryant H U. Selective estrogen receptor modulators. Drug News Perspect 8: 531-539, 1995.

The invention claimed is:

1. A method of treating sexual dysfunction comprising orally administering a therapeutically effective amount of ospemifene or a pharmaceutically acceptable salt thereof to a patient in need thereof in connection with the intake of a foodstuff having nutritional value and causing secretion of bile acids to enhance bioavailability of the ospemifene or pharmaceutically acceptable salt thereof.

2. The method according to claim 1 wherein the ospemifene or pharmaceutically acceptable salt thereof is administered at a time point which is in the range defined by 1 hour before starting the food intake and 2 hours after starting the food intake.

3. The method according to claim 2 wherein the ospemifene or pharmaceutically acceptable salt thereof is administered at a time point which is in the range defined to begin at a time point during the food intake and to end 1 hour after the food intake was started.

4. The method according to claim 3 wherein the ospemifene or pharmaceutically acceptable salt thereof is administered at a time point which is no later than 0.5 hours after starting the food intake.

5. The method according to claim 2 wherein the ospemifene or pharmaceutically acceptable salt thereof is administered in oral dosage form and wherein the dosage amount is from 30 to 90 mg/day.

6. The method according to claim 5 wherein the dosage amount is 60 mg.

7. The method of claim 2 wherein said patient is a perimenopausal or postmenopausal woman.

8. The method according to claim 1 wherein said sexual dysfunction is dyspareunia.

9. The method according to claim 8 wherein the ospemifene or pharmaceutically acceptable salt thereof is administered in oral dosage form and wherein the dosage amount is from 30 to 90 mg/day.

10. The method according to claim 9 wherein the dosage amount is 60 mg.

11. The method of claim 10 where said patient is a perimenopausal or postmenopausal woman.

12. The method according to claim 1 wherein the ospemifene or pharmaceutically acceptable salt thereof is administered in oral dosage form and wherein the dosage amount is from 30 to 90 mg/day.

13. The method according to claim 12 wherein the dosage amount is 60 mg.

14. The method of claim 1 wherein said patient is a perimenopausal or a postmenopausal woman.

15. A method of treating sexual dysfunction comprising orally administering a therapeutically effective amount of ospemifene to a patient in need thereof in connection with the intake of a foodstuff having nutritional value and causing secretion of bile acids to enhance bioavailability of the ospemifene or pharmaceutically acceptable salt thereof.

16. The method according to claim 15, wherein the ospemifene is administered at a time point which is in the range defined by 1 hour before starting the food intake and 2 hours after starting the food intake.

17. The method according to claim 15, wherein said sexual dysfunction is dyspareunia.

18. The method according to claim 17, wherein the dosage amount is 60 mg.

19. The method of claim 17, wherein said patient is a perimenopausal or a postmenopausal woman.

\* \* \* \* \*